United States Patent [19]

Jahn et al.

[11] Patent Number: 4,761,172

[45] Date of Patent: Aug. 2, 1988

[54] HERBICIDAL CYCLOHEXANOL DERIVATIVES, COMPOSITIONS, AND METHOD OF USE THEREFOR

[75] Inventors: Dieter Jahn, Edingen-Neckarhausen; Rainer Becker, Bad Durkheim; Michael Keil, Freinsheim; Ulrich Schirmer, Heidelberg; Winfried Richarz, Stockstadt; Bruno Wuerzer, Otterstadt; Norbert Meyer, Ladenburg, all of Fed. Rep. of Germany

[73] Assignee: BASF Aktiengesellschaft, Ludwigshafen, Fed. Rep. of Germany

[21] Appl. No.: 658,432

[22] Filed: Oct. 5, 1984

[30] Foreign Application Priority Data

Oct. 5, 1983 [DE] Fed. Rep. of Germany ....... 3336140
Nov. 25, 1983 [DE] Fed. Rep. of Germany ....... 3342630

[51] Int. Cl.⁴ .................... A01N 43/16; A01N 43/18; C07D 309/02; C07D 335/02
[52] U.S. Cl. .................................... 71/88; 71/90; 71/91; 71/115; 549/13; 549/419; 549/420; 549/425
[58] Field of Search ................. 549/13, 419, 420, 425; 71/88, 90, 91, 115

[56] References Cited

U.S. PATENT DOCUMENTS 3,989,737 11/1976 Sawaki et al. .................... 260/472
4,422,864 12/1983 Becker et al. ....................... 549/13

FOREIGN PATENT DOCUMENTS 0082694 6/1983 European Pat. Off. ............. 71/115
0104876 4/1984 European Pat. Off. ............. 71/115
2110673 6/1983 United Kingdom .................. 71/115

OTHER PUBLICATIONS

Sawaki et al., C.A. vol. 82 (1975), 82: 170218n, p. 477.
Chemical Abstracts, vol. 86, p. 397, No. 16357h (1977).

*Primary Examiner*—Alan L. Rotman
*Assistant Examiner*—J. G. Mullins
*Attorney, Agent, or Firm*—Keil & Weinkauf

[57] ABSTRACT

Cyclohexenol derivatives of the formula

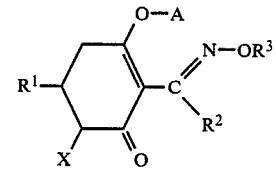

where $R^1$, $R^2$, $R^3$, X and A have the meanings stated in the description, are used for controlling undesirable plant growth.

15 Claims, No Drawings

HERBICIDAL CYCLOHEXANOL DERIVATIVES, COMPOSITIONS, AND METHOD OF USE THEREFOR

The present invention relates to cyclohexenol derivatives and to herbicides which contain these compounds as active ingredients.

It has been disclosed that cyclohexenol derivatives can be used for controlling undesirable grasses in broad-leaved crops (German Laid-Open Application DOS No. 2,461,027).

We have found that cyclohexenol derivatives of the formula

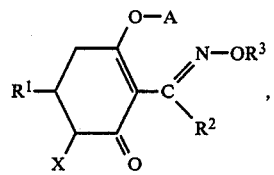

(I)

where $R^1$ is a 5-membered, 6-membered or 7-membered heterocyclic structure which contains 1 or 2 heteroatoms or ring members from the group consisting of N, O, S, SO and $SO_2$ and can be unsubstituted or substituted by not more than 2 alkyl or alkoxy groups, or cycloalkyl of 3 to 12 carbon atoms which is unsubstituted or substituted by not more than 3 methyl groups and may contain not more than 3 double bonds, or a bicyclic ring system which contains not more than 12 ring members and may contain not more than 2 double bonds and not more than 2 atoms from the group consisting of S and O, or a radical of the general structural formula B—Y—C—, where B is alkyl, alkoxyalkyl or an unsubstituted or halogen-substituted phenyl or benzyl radical, Y is oxygen or sulfur and C is an alkylene chain of not more than 4 carbon atoms, with the proviso than when B is alkyl, Y is sulfur and C is an alkylene chain, then A is not benzoyl, benzenesulfonyl, alkanoyl or alkenoyl, or alkyl, or phenyl which is unsubstituted or substituted by not more than 3 substituents from the group consisting of halogen, alkyl, alkoxy, alkylsulfonyl and nitro, with the proviso that when $R^1$ is alkylphenyl, furyl, thienyl or substituted phenyl, then A is not alkylsulfonyl, alkanoyl, aroyl, arylsulfonyl, phenoxyacetyl, alkyl or benzyl, X is hydrogen or methoxycarbonyl, $R^2$ is alkyl of 1 to 4 carbon atoms, $R^3$ is alkyl of 1 to 3 carbon atoms, alkenyl of 3 or 4 carbon atoms, haloalkenyl of 3 or 4 carbon atoms and 1 to 3 halogen substituents, or propargyl, and A is a radical of the general structure DE, where D is methylene, CO or $SO_2$ and E is an alkyl or alkenyl radical of not more than 20 carbon atoms, unsubstituted or methyl-substituted cycloalkyl of not more than 6 carbon atoms, or styryl, or is a phenyl or benzyl radical which is unsubstituted or substituted by not more than 3 substituents from the group consisting of halogen, alkyl, alkoxy and nitro, or is a 1-methylbenzyl or 1,1-dimethylbenzyl radical which is unsubstituted or substituted by halogen or methoxy, or is haloalkyl of not more than 3 carbon atoms and 3 halogen atoms, alkoxymethyl, acetoxymethyl or alkoxycarbonylalkyl, or is phenoxyalkylene which is unsubstituted or substituted in the phenoxy moiety by not more than 3 substituents from the group consisting of halogen, alkyl, alkoxy and methylsulfonyl, and which possesses a straight-chain or branched alkylene chain of not more than 5 carbon atoms, or E is a heterocyclic structure which contains 5 or 6 ring members and 1 or 2 heteroatoms from the group consisting of N, O and S and can be unsubstituted or substituted by halogen, alkyl, alkoxy, amino or dialkylamino, or is heteroarylalkyl, or A is a radical of the formula

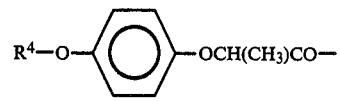

where $R^4$ is a phenyl, pyridyl, benzothiazolyl, benzoxazolyl, quinoxalinyl or quinolyl radical which is substituted by trifluoromethyl, halogen or alkyl, or A is a radical of the formula

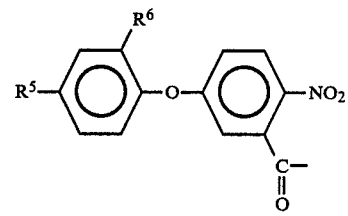

where $R^5$ and $R^6$ are each halogen or $CF_3$, or

A is a radical of the formula

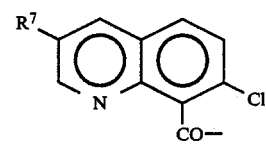

where $R^7$ is halogen or lower alkyl or

A is a radical of the formula

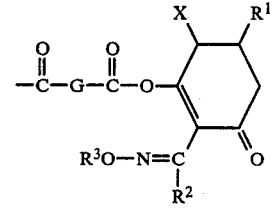

where G is phenylene or an alkylene chain of not more than 6 carbon atoms, or

A is a radical of the formula

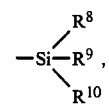

where $R^8$, $R^9$ and $R^{10}$ independently of one another are each alkyl or phenyl, or A is a radical of the formula

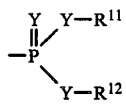

where the radicals Y independently of one another are each oxygen or sulfur, and $R^{11}$ and $R^{12}$ are each lower alkyl, possess herbicidal activity. Depending on the spectrum of plants to be controlled and on the toleration by crop plants, they either are selective herbicides or are used generally for controlling and inhibiting undesirable vegetation, including inhibition of the growth of vegetative and generative parts of crop plants, where these are useless, a hindrance or even disadvantageous.

In formula I, $R^1$ is a 5-membered, 6-membered or 7-membered heterocyclic structure which contains 1 or 2 heteroatoms or ring members from the group consisting of N, O, S, SO and $SO_2$ and can be unsubstituted or substituted by not more than 2 alkyl or alkoxy groups, such as pyridyl, pyrimidyl, 5,6-dihydro-2H-pyranyl, tetrahydropyranyl, 5,6-dihydro-2H-thiopyranyl, tetrahydrothiopyranyl, 1-oxotetrahydrothiopyranyl, 1,1-dioxotetrahydrothiopyranyl, tetrahydrofuryl, tetrahydrothienyl or 1,3-dioxepanyl radicals, eg. pyrid-2-yl, pyrid-3-yl, pyrid-4-yl, pyrimid-5-yl, 4,6-dimethoxypyrimid-5-yl, 5,6-dihydro-2H-pyran-3-yl, tetrahydropyran-3-yl, 5,6-dihydro-2H-thiopyran-3-yl, tetrahydrothiopyran-3-yl, 1-oxotetrahydrothiopyran-3-yl, 1,1-dioxotetrahydrothiopyran-3-yl, tetrahydrofur-3-yl, tetrahydrothien-3-yl, 2,6-dimethyltetrahydropyran-3-yl, 2,6-dimethyltetrahydrothiopyran-3-yl, 6-methoxytetrahydropyran-3-yl, 1,3-dioxepan-5-yl, 2-i-propyl-1,3-dioxepan-5-yl or benzo-1,3-dioxol-5-yl.

$R^1$ can furthermore be cycloalkyl of 3 to 12 carbon atoms which is unsubstituted or substituted by not more than 3 methyl groups and may contain not more than 3 double bonds, eg. cyclopropyl, cyclohexyl, cyclooctyl, cyclododecyl, cyclohex-b 3-enyl, cyclohex-1-enyl, 2-methylcyclohex-1-enyl, 4-methylcyclohex-3-enyl, 2,6,6-trimethylcyclohex-1-enyl, 2,6,6-trimethylcyclohex-2-enyl or cyclododeca-4,8-dienyl; a bicyclic ring system which contains not more than 12 ring members and may contain not more than 2 double bonds and not more than 2 atoms from the group consisting of S and O, eg. 4a,7,8,8a-tetrahydro-2H,5H-pyrano[4,3-b]pyran-3-yl, 3,4,4a,7,8,8a-hexahydro-2H,5H-pyrano[4,3-b]pyran-3-yl or 2,6,6-trimethylbicyclo[3,1,1]hept-3-yl; a radical of the general structural formula B—Y—C—, where B is $C_1-C_4$-alkyl, $C_1-C_4$-alkoxyalkyl or an unsubstituted or halogen-substituted phenyl or benzyl radical, Y is oxygen or sulfur and C is an alkylene chain of not more than 4 carbon atoms, eg. 2-ethylthio-n-propyl, 2-(chlorobenzyl)-thioethyl, 2-methoxy-n-propyl, 1-methyl-2-methoxyethyl or 1-(2-n-butoxyethoxy)-ethyl; $C_1-C_4$-alkyl; or phenyl which is unsubstituted or substituted by not more than 3 substituents from the group consisting of halogen, $C_1-C_4$-alkyl, $C_1-C_4$-alkoxy, $C_1-C_4$-alkylsulfonyl and nitro, eg. 4-methylphenyl, 4-ethylphenyl, 4-methoxyphenyl, 3-methylphenyl, 4-methylsulfonylphenyl or 3,4-dimethoxyphenyl.

In formula I, $R^2$ is straight-chain or branched alkyl of 1 to 4 carbon atoms, ie. methyl, ethyl, n-propyl, i-propyl, n-butyl, sec.-butyl, i-butyl or tert.-butyl.

In formula I, $R^3$ is propargyl, alkyl of 1 to 3 carbon atoms, alkenyl of 3 or 4 carbon atoms or haloalkenyl of 3 or 4 carbon atoms which can contain not more than three halogen substituents, eg. methyl, ethyl, n-propyl, i-propyl, n-butyl, sec.-butyl, i-butyl, tert.-butyl, allyl, 1-chloroprop-1-en-3-yl, 2-chloroprop-1-en-3-yl, 1,3-dichloroprop-1-en-3-yl or 1,1,2-trichloroprop-1-en-3-yl.

A can be a radical of the general structure DE, where D is methylene, CO or $SO_2$ and E is alkyl or alkenyl of not more than 20 carbon atoms, in particular not more than 18 carbon atoms.

A is therefore, for example, ethyl, propyl, acetyl, pivaloyl, butyryl, lauroyl, palmitoyl, stearyl, oleoyl, methylsulfonyl, ethylsulfonyl, propylsulfonyl or butylsulfonyl.

E can furthermore be unsubstituted or methylsubstituted cycloalkyl of 3 to 6 carbon atoms, eg. cyclopropyl, methylcyclopropyl, cyclobutyl, cyclopentyl, cyclohexyl or methylcyclohexyl; a phenyl, benzyl, 1-methylbenzyl or 1,1-dimethylbenzyl radical which is substituted by not more than 3 substituents from the group consisting of halogen, $C_1-C_4$-alkyl, $C_1-C_4$-alkoxy, amino and nitro, eg. methylphenyl, methoxyphenyl, nitrophenyl, dichloromethoxyphenyl, trichlorophenyl, benzyl, fluorobenzyl, chlorobenzyl, methoxybenzyl, α-methylbenzyl, α-methylchlorobenzyl, α-methylbromobenzyl, α-methylmethoxybenzyl, α,α-dimethylbenzyl or α,α-dimethylchlorobenzyl; haloalkyl of not more than 3 halogen atoms and 3 carbon atoms, eg. chloromethyl, dichloromethyl, trichloromethyl, fluoromethyl, trifluoromethyl or 1,1-dichloroethyl; $C_1-C_4$-alkoxymethyl, acetoxymethyl or alkoxycarbonylalkyl of, in total, 3 to 9 carbon atoms, eg. methoxymethyl, ethoxymethyl, butoxymethyl, ethoxycarbonylmethyl or ethoxycarbonylethyl; phenoxyalkylene which is unsubstituted or substituted in the phenoxy moiety by not more than 3 substituents from the group consisting of halogen, $C_1-C_4$-alkyl and $C_1-C_4$-alkoxy, eg. phenoxymethyl, chlorophenoxymethyl, dichlorophenoxymethyl, chloromethylphenoxymethyl, trichlorophenoxymethyl, methylphenoxyethyl, dichlorophenoxyethyl, chloromethylphenoxyethyl, trichlorophenoxyethyl, chlorophenoxypropyl or dichlorophenoxypropyl; or an unsubstituted or substituted heterocyclic radical which has 5 or 6 ring members and 1 or 2 heteroatoms from the group consisting or N, O and S, eg. furyl, methylfuryl, dimethylfuryl, isoxazolyl, methylisoxazolyl, thienyl, pyridyl, chloropyridyl or dichloropyridyl.

A can furthermore be a radical of the formula

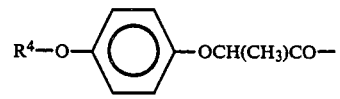

where $R^4$ is a phenyl, pyridyl, benzothiazolyl, benzoxazolyl, quinoxalinyl or quinolyl radical which is substituted by trifluoromethyl, halogen or alkyl, examples of $R^4$ being dichlorophenyl, trifluoromethylphenyl, trifluoromethylpyridyl, chlorotrifluoromethylpyridyl, dichloropyridyl, iodopyridyl, chloroquinoxalinyl, chlorobenzothiazolyl or chlorobenzoxazolyl;

a radical of the formula

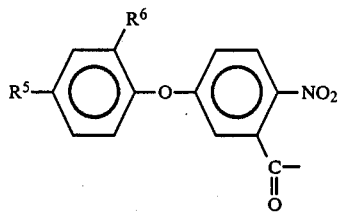

where $R^5$ is, for example, trifluoromethyl, chlorine or bromine and $R^6$ is, for example, fluorine, chlorine or bromine;

a radical of the formula

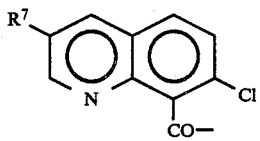

where $R^7$ can be chlorine, bromine, methyl or ethyl;

a radical of the formula

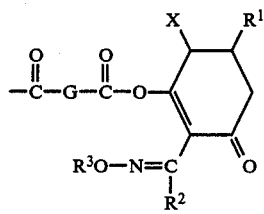

where G is phenylene, methylene, ethylene, propylene, tetramethylene, pentamethylene, hexamethylene or heptamethylene, and $R^1$, $R^2$ and $R^3$ have the above meanings;

a radical of the formula

where $R^8$, $R^9$ and $R^{10}$ independently of one another are each alkyl or phenyl, examples of $R^8$, $R^9$ and $R^{10}$ being methyl, ethyl, n-propyl, i-propyl, n-butyl, i-butyl, sec.-butyl, tert.-butyl and phenyl; or a radical of the formula

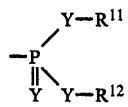

where the radicals Y independently of one another are each oxygen or sulfur, and $R^{11}$ and $R^{12}$ are each $C_1$–$C_4$-alkyl, such as methyl, ethyl, n-propyl or i-propyl.

Preferred cyclohexenol derivatives of the formula I are those in which $R^1$ is a 6-membered heterocyclic structure, in particular one which contains one heteroatom or ring member from the group consisting of O, S, SO or $SO_2$. Examples of appropriate radicals are tetrahydropyranyl, tetrahydrothiopyranyl, 1-oxotetrahydrothiopyranyl and 1,1-dioxotetrahydrothiopyranyl, in particular tetrahydropyran-3-yl, tetrahydrothiopyran-3-yl, 1-oxotetrahydrothiopyran-3-yl and 1,1-dioxotetrahydrothiopyran-3-yl. Other preferred cyclohexenol derivatives of the formula I are those in which X is hydrogen.

Cyclohexenol derivatives of the formula I can be obtained by a method in which a compound of the formula

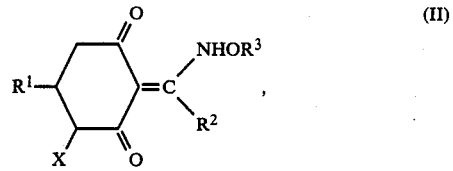

where $R^1$, $R^2$, $R^3$ and X have the meanings stated for formula I, is reacted with a compound of the formula A—Z, where A has the above meanings and Z is halogen or tosyl. The reaction is carried out in an inert solvent, in the presence of a base at from $-5°$ C. to the boiling point of the mixture. If necessary, the base can be employed in aqueous solution. Depending on the miscibility, the reaction is then carried out in the homogeneous phase or in a two-phase system. In the latter case, the reaction can be accelerated by using a phase-transfer catalyst, such as an ammonium or phosphonium salt.

The reaction can also be accelerated by using an azole, such as imidazole or pyrazole, or pyridine or its derivatives, eg. 4-piperidinopyridine or 4-dimethylaminopyridine.

Suitable solvents are dimethyl sulfoxide, dimethylformamide, benzene, toluene, hydrocarbons and chlorohydrocarbons, eg. chloroform, dichloromethane, dichloroethane, hexane or cyclohexane, ketones, eg. acetone or butanone, esters, eg. ethyl acetate, and ethers, eg. diethyl ether, dioxane or tetrahydrofuran.

Examples of suitable bases are carbonates, bicarbonates, acetates, alcoholates, hydroxides and oxides of alkali metals and alkaline earth metals, in particular of sodium, potassium, magnesium and calcium. Organic bases, such as pyridine or tertiary amines, can also be used.

Salts of compounds of the formula II can also be used as starting materials for the synthesis of the novel compounds. In this case, the reaction is carried out in the manner described above, but without the addition of a base.

Compounds of the formula II are obtained by conventional processes:

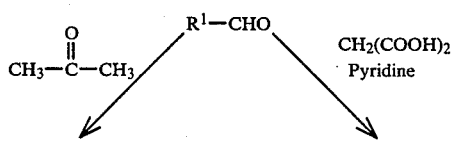

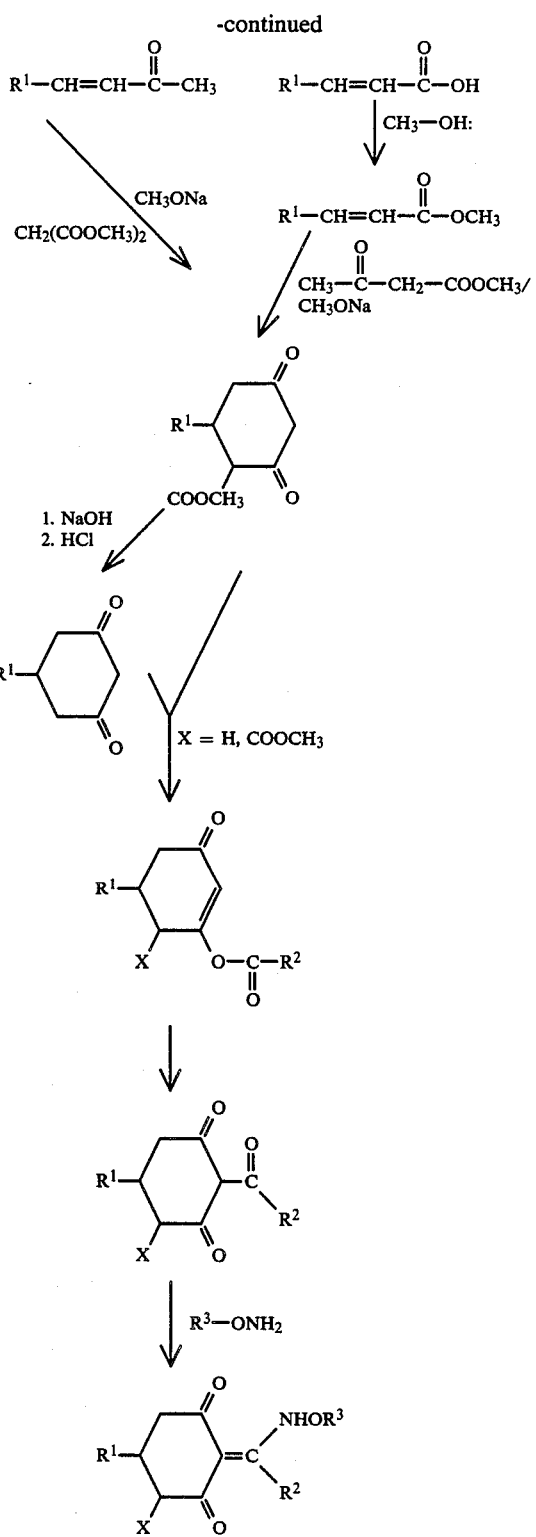

The Examples which follow illustrate the preparation of the novel cyclohexenol derivatives of the formula I.

In the Examples, parts by weight bear the same relation to parts by volume as that of the kilogram to the liter.

The $^1$H-NMR data are given as $\delta$ values (ppm) and are based on tetramethylsilane as an internal standard. The solvent used as CDCl$_3$. Abbreviations for the signal structures are as follows: s=singlet, d=doublet, t=triplet, q=quartet, m=multiplet, strongest signal.

EXAMPLE 1

3.1 parts by weight of 2-ethoxyaminobutylidene-5-(tetrahydropyran-3-yl)-cyclohexane-1,3-dione, 1,2 parts by weight of triethylamine and 0.2 part by weight of 4-dimethylaminopyridine in 50 parts by volume of dichloromethane are cooled to 0° C., and 1.4 parts by weight of benzoyl chloride are added dropwise to this solution at from 0° to 5° C. The mixture is then allowed to reach room temperature, after which it is stirred for a further hour, washed with 10 percent strength hydrochloric acid and twice with 5 percent strength sodium hydroxide solution and water, and dried over sodium sulfate, and the solvent is distilled off. 1-Benzoyloxy-2-(N-ethoxybutyrimidoyl)-5-(tetrahydro-pyran-3-yl)-cyclohex-1-en-3-one are obtained as an oil (active ingredient no. 1)

$^1$H-NMR spectrum: 0.92 (t), 3.95 (t), 7.65 (m).

EXAMPLE 2

8.0 parts by weight of 2-ethoxyaminobutyldiene-5-(tetrahydropyran-3-yl)-cyclohexane-1,3-dione are dissolved in 50 parts by volume of acetone, after which 1.1 parts by weight of sodium hydroxide in 5 parts by volume of water are added, the mixture is stirred for 30 minutes and then cooled to 0° C., and 2.2 parts by weight of acetyl chloride are added dropwise at this temperature. Thereafter, the mixture is stirred for 2 hours at room temperature, the solvent is distilled off under reduced pressure, the residue is dissolved in methylene chloride, the insoluble constituents are filtered off, the solution is extracted twice with 5 percent strength sodium hydroxide solution, washed neutral with water and dried over magnesium sulfate and the solvent is distilled off under reduced pressure. 1-Acetoxy-2-(N-ethoxybutyrimidoyl)-5-(tetrahydropyran-3-yl)-cyclohex-1-en-3-one is obtained as an oil (active ingredient no. 2).

$^1$H-NMR spectrum: 0.95 (t), 1.30 (t), 2.20 (s), 4.15 (q).

EXAMPLE 3

6.5 parts by weight of the sodium salt of 2-ethoxyaminobutylidene-5-(pyrid-3-yl)-cyclohexane-1,3-dione are suspended in dichloromethane, and 1.6 parts by weight of acetyl chloride are added dropwise to the suspension at room temperature. Stirring is continued for 2 hours, after which the mixture is washed with 5 percent strength sodium hydroxide solution and water and dried over sodium sulfate, and the solvent is distilled off under reduced pressure. 1-Acetoxy-2-(N-ethoxybutyrimidoyl)-5-(pyrid-3-yl)-cyclohex-1-en-1-one is obtained as a viscous oil (active ingredient no. 3).

$^1$H-NMR data: 1.0 (t), 4.0 (q), 8.6 (m).

The following compounds of the formula I are obtained in a similar manner:

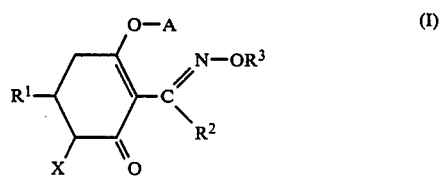

| Compound no. | R¹ | X | R² | R³ | A | ¹H—NMR data |
|---|---|---|---|---|---|---|
| 4 | tetrahydropyran-3-yl | H | n-propyl | ethyl | 4-methoxybenzoyl | 0.85 (t), 3.90 (s), 7.0 (d) |
| 5 | tetrahydropyran-3-yl | H | n-propyl | ethyl | 2-methylbenzoyl | 0.88 (t), 1.10 (t), 8.0 (d) |
| 6 | tetrahydropyran-3-yl | H | n-propyl | ethyl | 4-tert.-butylbenzoyl | 1.40 (s), 4.0 (q), 7.50 (d) |
| 7 | tetrahydropyran-3-yl | H | n-propyl | ethyl | 4-chlorobenzoyl | 0.90 (t), 4.0 (q), 7.50 (d) |
| 8 | tetrahydropyran-3-yl | H | n-propyl | ethyl | 4-nitrobenzoyl | 3.95 (q), 8.40 (m) |
| 9 | tetrahydropyran-3-yl | H | n-propyl | ethyl | butyryl | 1.25 (t), 1.90 (m), 3.35 (m) |
| 10 | tetrahydropyran-3-yl | H | n-propyl | ethyl | benzene sulfonyl | 1.82 (t), 3.4 (m), 6.62 (d) |
| 11 | tetrahydropyran-3-yl | H | n-propyl | ethyl | ethylsulfonyl | 0.92 (t), 3.35 (q), 4.10 (q) |
| 12 | tetrahydropyran-3-yl | H | n-propyl | ethyl | methylsulfonyl | 0.90 (t), 3.20 (s), 4.10 (q) |
| 13 | tetrahydropyran-3-yl | H | n-propyl | ethyl | phenylacetyl | 1.60 (m), 3.75 (s), 7.30 (m) |
| 14 | tetrahydropyran-3-yl | H | n-propyl | ethyl | 3,5-dichlorobenzoyl | 0.87 (t), 7.65 (m), 7.95 (m) |
| 15 | tetrahydropyran-3-yl | H | n-propyl | ethyl | chloroacetyl | 0.92 (t), 4.0 (s) |
| 16 | tetrahydropyran-3-yl | H | n-propyl | ethyl | 2,5-dichloro-6-methoxybenzoyl | 0.90 (t), 1.65 (m), 7.42 (d) |
| 17 | tetrahydropyran-3-yl | H | n-propyl | ethyl | 3,5-dimethylbenzoyl | 1.10 (t), 2.38 (s), 3.30 (m) |
| 18 | tetrahydropyran-3-yl | H | n-propyl | ethyl | pivaloyl | 0.88 (t), 1.26 (s), 4.10 (q) |
| 19 | tetrahydropyran-3-yl | H | n-propyl | ethyl | lauroyl | |
| 20 | tetrahydropyran-3-yl | H | n-propyl | ethyl | palmitoyl | 1.25 (m), 2.40 (m), 4.10 (q) |
| 21 | tetrahydropyran-3-yl | H | n-propyl | ethyl | stearoyl | 0.90 (t), 1.30 (m), 4.10 (q) |
| 22 | tetrahydropyran-3-yl | H | n-propyl | ethyl | oleoyl | 0.86 (t), 1.25 (m), 5.40 (t) |
| 23 | tetrahydropyran-3-yl | H | n-propyl | ethyl | (4-methoxyphenyl)-acetyl | |
| 24 | tetrahydropyran-3-yl | H | n-propyl | ethyl | 2-(4-methoxyphenyl)-propionyl | 0.84 (t), 6.95 (m), 3.82 (s) |
| 25 | tetrahydropyran-3-yl | H | n-propyl | ethyl | 2-(4-chloro-2-methyl-phenoxy)-propionyl | 1.25 (t), 4.85 (q), 7.15 (m) |
| 26 | tetrahydropyran-3-yl | H | n-propyl | ethyl | 4-(2,4-dichloro-phenoxy)-butyryl | 1.60 (m), 2.17 (m), 7.18 (m) |
| 27 | tetrahydropyran-3-yl | H | n-propyl | ethyl | 2-methyl-2-phenyl-propionyl | 0.80 (t), 3.12 (m), 7.36 (m) |
| 28 | tetrahydropyran-3-yl | H | n-propyl | ethyl | methoxyacetyl | 1.65 (m), 2.65 (m), 3.45 (s) |
| 29 | tetrahydropyran-3-yl | H | n-propyl | ethyl | acetoxyacetyl | 1.65 (m), 2.20 (s), 4.15 (q) |
| 30 | tetrahydropyran-3-yl | H | n-propyl | ethyl | 4-methoxysuccinyl | 1.25 (t), 2.70 (m), 3.70 (s) |
| 31 | tetrahydropyran-3-yl | H | n-propyl | ethyl | 2,5-dimethyl-3-furylcarbonyl | 1.16 (t), 2.26 (s), 4.05 (q) |
| 32 | tetrahydropyran-3-yl | H | n-propyl | ethyl | 3,5-dimethyl-4-isoxazolylcarbonyl | 0.83 (t), 2.64 (s), 4.00 (q) |
| 33 | tetrahydropyran-3-yl | H | n-propyl | ethyl | 5-isoxazolylcarbonyl | 2.75 (m), 7.10 (m), 8.55 (m) |
| 34 | tetrahydropyran-3-yl | H | n-propyl | ethyl | 3-pyridylcarbonyl | |
| 35 | tetrahydropyran-3-yl | H | n-propyl | ethyl | 2-chloro-3-pyridyl-carbonyl | 0.86 (t), 7.3 (m), 8.5 (m) |
| 36 | tetrahydropyran-3-yl | H | n-propyl | ethyl | 3,6-dichloro-2-pyridylcarbonyl | |
| 37 | tetrahydropyran-3-yl | H | n-propyl | ethyl | thien-2-yl-acetyl | 1.28 (m), 3.98 (s), 7.00 (m) |
| 38 | tetrahydropyran-3-yl | H | n-propyl | ethyl | cinnamoyl | 3.18 (q), 6.48 (d), 7.75 (d) |
| 39 | tetrahydropyran-3-yl | H | n-propyl | ethyl | cyclopropylcarbonyl | 1.25 (t), 2.55 (m), 4.10 (q) |
| 40 | tetrahydropyran-3-yl | H | n-propyl | ethyl | 1-Methyl-cyclo-propyl-carbonyl | 0.82 (m), 1.30 (s), 3.20 (q) |
| 41 | tetrahydropyran-3-yl | H | n-propyl | ethyl | 2,2-dichloropropionyl | |
| 42 | tetrahydropyran-3-yl | H | n-propyl | ethyl | n-butylsulfonyl | 1.25 (t), 3.90 (m), 4.15 (q) |
| 43 | tetrahydropyran-3-yl | H | n-propyl | ethyl | 3-(2-chloro-4-tri-fluoromethylphenoxy)-6-nitrobenzoyl | |
| 44 | tetrahydropyran-3-yl | H | ethyl | ethyl | 3-(2-chloro-4-tri-fluoromethylphenoxy)-6-nitrobenzoyl | |
| 45 | tetrahydropyran-3-yl | H | ethyl | allyl | 3-(2-chloro-4-tri-fluoromethylphenoxy)-6-nitrobenzoyl | |
| 46 | tetrahydropyran-3-yl | H | n-propyl | ethyl | 2-[4-(4-trifluoromethyl-phenoxy)-phenoxy]-propionyl | |
| 47 | tetrahydropyran-3-yl | H | n-propyl | ethyl | 2-[4-(4-iodopyrid-2-yl-oxy)-phenoxy]-propionyl | |
| 48 | tetrahydropyran-3-yl | H | n-propyl | ethyl | 2-[4-(4-trifluoromethyl-pyrid-2-yloxy)-phenoxyl]-propionyl | |
| 49 | tetrahydropyran-3-yl | H | n-propyl | ethyl | 2-[4-(4-trifluoromethyl-6-chloropyrid-2-yloxy)-phenoxy]-propionyl | |
| 50 | tetrahydropyran-3-yl | H | n-propyl | ethyl | 2-[4-(6-chloro-2-quin-oxalinoxy)-phenoxy]-propionyl | |
| 51 | tetrahydropyran-3-yl | H | n-propyl | ethyl | 2[4-(6-chlorobenzthiazol-2-yloxy)-phenoxy]-propionyl | |
| 52 | tetrahydropyran-3-yl | H | n-propyl | ethyl | 2-[4-(5-chlorobenzoxazol-2-yloxy)-phenoxy]- | |

-continued

| Compound no. | R¹ | X | R² | R³ | A | ¹H—NMR data |
|---|---|---|---|---|---|---|
| | | | | | propionyl | |
| 53 | tetrahydropyran-3-yl | H | n-propyl | n-propyl | benzoyl | 0.75 (t), 2.6 (m), 7.6 (m) |
| 54 | tetrahydropyran-3-yl | H | n-propyl | n-propyl | 2-methylbenzoyl | |
| 55 | tetrahydropyran-3-yl | H | n-propyl | methyl | benzoyl | 0.85 (t), 3.70 (s), 7.6 (m) |
| 56 | tetrahydropyran-3-yl | H | n-propyl | propargyl | benzoyl | 0.86 (t), 4.46 (d), 7.45 (m) |
| 57 | tetrahydropyran-3-yl | H | n-propyl | 3-chloro-allyl | benzoyl | 1.65 (m), 4.45 (d), 8.10 (d) |
| 58 | 2-ethylthio-n-propyl | H | n-propyl | ethyl | butyryl | |
| 59 | 2-ethylthio-n-propyl | H | n-propyl | ethyl | acetyl | |
| 60 | 2-ethylthio-n-propyl | H | n-propyl | ethyl | benzyl | 0.86 (t), 4.15 (q), 5.1 (s) |
| 61 | 2-ethylthio-n-propyl | H | n-propyl | ethyl | methylsulfonyl | 0.92 (t), 1.35 (d), 3.15 (s) |
| 62 | 2-ethylthio-n-propyl | H | n-propyl | ethyl | phenylacetyl | 1.6 (t), 4.1 (q), 7.32 (m) |
| 63 | 2-ethylthio-n-propyl | H | n-propyl | ethyl | 3,5-dichlorobenzoyl | |
| 64 | 2-ethylthio-n-propyl | H | n-propyl | ethyl | chloroacetyl | |
| 65 | 2-ethylthio-n-propyl | H | n-propyl | ethyl | 2,5-dichloro-6-methoxybenzoyl | |
| 66 | 2-ethylthio-n-propyl | H | n-propyl | ethyl | 3,5-dimethylbenzoyl | |
| 67 | 2-ethylthio-n-propyl | H | n-propyl | ethyl | pivaloyl | |
| 68 | 2-ethylthio-n-propyl | H | n-propyl | ethyl | stearoyl | |
| 69 | 2-ethylthio-n-propyl | H | n-propyl | ethyl | oleoyl | |
| 70 | 2-ethylthio-n-propyl | H | n-propyl | ethyl | (4-methoxyphenyl)-acetyl | |
| 71 | 2-ethylthio-n-propyl | H | n-propyl | ethyl | 2-(4-methoxyphenyl)-propionyl | 1.27 (m), 3.82 (s), 6.9 (d) |
| 72 | 2-ethylthio-n-propyl | H | n-propyl | ethyl | 2-(4-chloro-2-methyl-phenoxy)-propionyl | 0.87 (t), 2.55 (m), 7.1 (m) |
| 73 | 2-ethylthio-n-propyl | H | n-propyl | ethyl | 4-(2,4-dichloro-phenoxy)-butyryl | 0.85 (t), 4.05 (m), 7.16 (m) |
| 74 | 2-ethylthio-n-propyl | H | n-propyl | ethyl | 2-methyl-2-phenyl-propionyl | 0.85 (t), 1.64 (s), 7.35 (m) |
| 75 | 2-ethylthio-n-propyl | H | n-propyl | ethyl | methoxyacetyl | |
| 76 | 2-ethylthio-n-propyl | H | n-propyl | ethyl | acetoxyacetyl | |
| 77 | 2-ethylthio-n-propyl | H | n-propyl | ethyl | 4-methoxysuccinyl | |
| 78 | 2-ethylthio-n-propyl | H | n-propyl | ethyl | 2,5-dimethyl-3-furylcarbonyl | |
| 79 | 2-ethylthio-n-propyl | H | n-propyl | ethyl | 3,5-dimethyl-isoxazol-4-yl-carbonyl | 2.45 (s), 2.6 (s), 4.02 (q) |
| 80 | 2-ethylthio-n-propyl | H | n-propyl | ethyl | 5-isoxazolylcarbonyl | |
| 81 | 2-ethylthio-n-propyl | H | n-propyl | ethyl | 3-pyridylcarbonyl | |
| 82 | 2-ethylthio-n-propyl | H | n-propyl | ethyl | 2-chloro-3-pyridyl-carbonyl | |
| 83 | 2-ethylthio-n-propyl | H | n-propyl | ethyl | 3,6-dichloro-2-pyridyl-carbonyl | |
| 84 | 2-ethylthio-n-propyl | H | n-propyl | ethyl | (2-thienyl)-acetyl | |
| 85 | 2-ethylthio-n-propyl | H | n-propyl | ethyl | pivaloyl | |
| 86 | 2-ethylthio-n-propyl | H | n-propyl | ethyl | cyclopropylcarbonyl | |
| 87 | 2-ethylthio-n-propyl | H | H | ethyl | (1-methyl)-cyclopropyl-carbonyl | |
| 88 | 2-ethylthio-n-propyl | H | H | ethyl | 2,2-dichloropropionyl | |
| 89 | 2-ethylthio-n-propyl | H | H | ethyl | n-butylsulfonyl | |
| 90 | 2-ethylthio-n-propyl | H | H | ethyl | 3-(2-chloro-4-trifluoro-methylphenoxy)-6-nitro-benzoyl | |
| 91 | 2-ethylthio-n-propyl | H | ethyl | ethyl | 3-(2-chloro-4-trifluoro-methylphenoxy)-6-nitro-benzoyl | |
| 92 | 2-ethylthio-n-propyl | H | ethyl | allyl | 3-(2-chloro-4-trifluoro-methylphenoxy)-6-nitro-benzoyl | |
| 93 | 2-ethylthio-n-propyl | H | n-propyl | ethyl | 2-[4-(4-trifluoromethyl-phenoxy)-phenoxy]-propionyl | |
| 94 | 2-ethylthio-n-propyl | H | n-propyl | ethyl | 2-[4-(4-iodopyrid-2-yl-oxy)-phenoxy]-propionyl | |
| 95 | 2-ethylthio-n-propyl | H | n-propyl | ethyl | 2-[4-(4-trifluoromethyl-pyrid-2-yl-oxy)-phenoxy]-propionyl | |
| 96 | 2-ethylthio-n-propyl | H | n-propyl | ethyl | 2-[4-(4-trifluoromethyl-6-chloropyrid-2-yloxy)-phenoxy]-propionyl | |
| 97 | 2-ethylthio-n-propyl | H | n-propyl | ethyl | 2-[4-(6-chloro-2-quin-oxalinoxy)-phenoxy]-propionyl | |
| 98 | 2-ethylthio-n-propyl | H | n-propyl | ethyl | 2-[4-(6-chlorobenzthiazol-2-yloxy)-phenoxy]-propionyl | |
| 99 | 2-ethylthio-n-propyl | H | n-propyl | ethyl | 2-[4-(5-chlorobenzoxazol-2-yloxy)-phenoxy]-propionyl | |
| 100 | 2-ethylthio-n-propyl | H | n-propyl | ethyl | lauroyl | |

-continued

| Compound no. | R¹ | X | R² | R³ | A | ¹H—NMR data |
|---|---|---|---|---|---|---|
| 101 | 2-ethylthio-n-propyl | H | n-propyl | ethyl | palmitoyl | |
| 102 | 2-ethylthio-n-propyl | H | n-propyl | ethyl | 2,4-phenoxyacetyl | |
| 103 | 2-ethylthio-n-propyl | H | n-propyl | ethyl | butyl-dimethyl-silyl | |
| 104 | 2-ethylthio-n-propyl | H | n-propyl | ethyl | O,O—diethylthiophosphoryl | 0.90 (t), 2.50 (m) |
| 105 | tetrahydrothiopyran-3-yl | H | n-propyl | ethyl | 4-methoxybenzoyl | |
| 106 | tetrahydrothiopyran-3-yl | H | n-propyl | ethyl | 2-methylbenzoyl | |
| 107 | tetrahydrothiopyran-3-yl | H | n-propyl | ethyl | 4-t-butylbenzoyl | |
| 108 | tetrahydrothiopyran-3-yl | H | n-propyl | ethyl | 4-chlorobenzoyl | |
| 109 | tetrahydrothiopyran-3-yl | H | n-propyl | ethyl | benzoyl | 0.95 (t), 3.95 (q), 7.60 (m) |
| 110 | tetrahydrothiopyran-3-yl | H | n-propyl | ethyl | butyryl | |
| 111 | tetrahydrothiopyran-3-yl | H | n-propyl | ethyl | benzenesulfonyl | |
| 112 | tetrahydrothiopyran-3-yl | H | n-propyl | ethyl | benzyl | |
| 113 | tetrahydrothiopyran-3-yl | H | n-propyl | ethyl | methylsulfonyl | |
| 114 | tetrahydrothiopyran-3-yl | H | n-propyl | ethyl | phenylacetyl | |
| 115 | tetrahydrothiopyran-3-yl | H | n-propyl | ethyl | 3,5-dichlorobenzoyl | |
| 116 | tetrahydrothiopyran-3-yl | H | n-propyl | ethyl | chloroacetyl | |
| 117 | tetrahydrothiopyran-3-yl | H | n-propyl | ethyl | 2,5-dichloro-6-methoxybenzoyl | |
| 118 | tetrahydrothiopyran-3-yl | H | n-propyl | ethyl | 3,5-dimethylbenzoyl | |
| 119 | tetrahydrothiopyran-3-yl | H | n-propyl | ethyl | pivaloyl | |
| 120 | tetrahydrothiopyran-3-yl | H | n-propyl | ethyl | lauroyl | |
| 121 | tetrahydrothiopyran-3-yl | H | n-propyl | ethyl | palmitoyl | |
| 122 | tetrahydrothiopyran-3-yl | H | ethyl | ethyl | stearoyl | 1.25 (s), 2.40 (t), 4.10 (q) |
| 123 | tetrahydrothiopyran-3-yl | H | n-propyl | ethyl | oleoyl | |
| 124 | tetrahydrothiopyran-3-yl | H | n-propyl | ethyl | (4-methoxyphenyl)-acetyl | |
| 125 | tetrahydrothiopyran-3-yl | H | n-propyl | ethyl | 2-(4-methoxyphenyl)-propionyl | |
| 126 | tetrahydrothiopyran-3-yl | H | n-propyl | ethyl | 2-(4-chloro-2-methyl-phenoxy)-propionyl | |
| 127 | tetrahydrothiopyran-3-yl | H | n-propyl | ethyl | 4-(2,4-dichlorophenoxy)-butyryl | |
| 128 | tetrahydrothiopyran-3-yl | H | n-propyl | ethyl | 2-methyl-2-phenyl-propionyl | |
| 129 | tetrahydrothiopyran-3-yl | H | n-propyl | ethyl | methoxyacetyl | |
| 130 | tetrahydrothiopyran-3-yl | H | n-propyl | ethyl | acetoxyacetyl | |
| 131 | tetrahydrothiopyran-3-yl | H | n-propyl | ethyl | 4-methoxysuccinyl | |
| 132 | tetrahydrothiopyran-3-yl | H | n-propyl | ethyl | 2,5-dimethyl-3-furylcarbonyl | |
| 133 | tetrahydrothiopyran-3-yl | H | n-propyl | ethyl | 3,5-dimethyl-4-isoxazolylcarbonyl | |
| 134 | tetrahydrothiopyran-3-yl | H | n-propyl | ethyl | 5-isoxazolylcarbonyl | |
| 135 | tetrahydrothiopyran-3-yl | H | n-propyl | ethyl | 3-pyridylcarbonyl | |
| 136 | tetrahydrothiopyran-3-yl | H | n-propyl | ethyl | 2-chloro-3-pyridyl-carbonyl | |
| 137 | tetrahydrothiopyran-3-yl | H | n-propyl | ethyl | 3,6-dichloro-2-pyridyl | |
| 138 | tetrahydrothiopyran-3-yl | H | n-prpoyl | ethyl | (2-thienyl)-acetyl | |
| 139 | tetrahydrothiopyran-3-yl | H | n-propyl | ethyl | pivaloyl | |
| 140 | tetrahydrothiopyran-3-yl | H | n-propyl | ethyl | cyclopropylcarbonyl | |
| 141 | tetrahydrothiopyran-3-yl | H | n-propyl | ethyl | 1-methyl-cyclo-propyl-carbonyl | |
| 142 | tetrahydrothiopyran-3-yl | H | n-propyl | ethyl | 2,2-dichloropropionyl | |
| 143 | tetrahydrothiopyran-3-yl | H | n-propyl | ethyl | n-butylsulfonyl | |
| 144 | tetrahydrothiopyran-3-yl | H | n-propyl | ethyl | 3-(2-chloro-4-trifluoro-methylphenoxy)-6-nitrobenzoyl | |
| 145 | tetrahydrothiopyran-3-yl | H | ethyl | ethyl | 3-(2-chloro-4-trifluoro-methylphenoxy)-6-nitro-benzoyl | |
| 146 | tetrahydrothiopyran-3-yl | H | ethyl | allyl | 3-(2-chloro-4-trifluoro-methylphenoxy)-6-nitro-benzoyl | |
| 147 | tetrahydrothiopyran-3-yl | H | n-propyl | ethyl | 2-[4-(4-trifluoromethyl-phenoxy)-phenoxy]-propionyl | 1.30 (t), 4.15 (q), 7.58 (t) |
| 148 | tetrahydrothiopyran-3-yl | H | n-propyl | ethyl | 2-[4-(4-iodopyrid-2-yl-oxy)-phenoxy]-propionyl | |
| 149 | tetrahydrothiopyran-3-yl | H | n-propyl | ethyl | 2-[4-(4-trifluoromethyl-pyrid-2-yloxy)-phenoxy]-propionyl | |
| 150 | tetrahydrothiopyran-3-yl | H | n-propyl | ethyl | 2-[4-(4-trifluoromethyl-6-chloropyrid-2-yloxy)-phenoxy]-propionyl | |
| 151 | tetrahydrothiopyran-3-yl | H | n-propyl | ethyl | 2-[4-(6-chloro-2-quin-oxalinoxy)-phenoxy]-propionyl | |
| 152 | tetrahydrothiopyran-3-yl | H | n-propyl | ethyl | 2-[4-(6-chlorobenzthiazol-2-yloxy)-phenoxy]-propionyl | |
| 153 | tetrahydrothiopyran-3-yl | H | n-propyl | ethyl | 2-[4-(6-chlorobenzoxazol-2-yloxy)-phenoxy]-propionyl | |

-continued

| Compound no. | R¹ | X | R² | R³ | A | ¹H—NMR data |
|---|---|---|---|---|---|---|
| 154 | tetrahydrothiopyran-3-yl | H | n-propyl | n-propyl | benzoyl | |
| 155 | tetrahydrothiopyran-3-yl | H | n-propyl | n-propyl | 2-methylbenzoyl | |
| 156 | tetrahydrothiopyran-3-yl | H | n-propyl | methyl | benzoyl | |
| 157 | tetrahydrothiopyran-3-yl | H | n-propyl | propargyl | benzoyl | |
| 158 | tetrahydrothiopyran-3-yl | H | n-propyl | 3-chloro-allyl | benzoyl | |
| 159 | tetrahydrothiopyran-3-yl | H | n-propyl | ethyl | 3,7-dichloroquino-lino-8-yl | |
| 160 | pyrid-3-yl | H | ethyl | ethyl | pivaloyl | 1.26 (s), 2.45 (m), 7.61 (d) |
| 161 | pyrid-3-yl | H | n-propyl | ethyl | benzoyl | 1.40 (m), 7.60 (m), 8.62 (m) |
| 162 | pyrid-3-yl | H | n-propyl | ethyl | oleyl | |
| 163 | pyrid-3-yl | H | n-propyl | ethyl | palmitoyl | 1.25 (s), 4.10 (q), 8.60 (m) |
| 164 | pyrid-3-yl | H | n-propyl | ethyl | 2-methyl-2-phenyl-propionyl | |
| 165 | pyrid-3-yl | H | n-propyl | ethyl | 3,5-dimethylbenzoyl | |
| 166 | pyrid-3-yl | H | ethyl | ethyl | 3,5-dimethylbenzoyl | |
| 167 | pyrid-3-yl | H | ethyl | ethyl | 4-(2,4-dichloro-phenoxy)-butyryl | |
| 168 | pyrid-3-yl | H | ethyl | ethyl | 2-(2-methyl-4-chloro-phenoxy)-propionyl | |
| 169 | pyrid-3-yl | H | methyl | ethyl | benzoyl | 1.40 (m), 7.60 (m), 8.62 (m) |
| 170 | pyrid-3-yl | H | ethyl | ethyl | 3-(2-chloro-4-trifluoro-methylphenoxy)-6-nitrobenzoyl | |
| 171 | pyrid-3-yl | H | n-propyl | ethyl | 3-(2-chloro-4-trifluoro-methylphenoxy)-6-nitrobenzoyl | |
| 172 | pyrid-3-yl | H | n-propyl | ethyl | 2-[4-(4-trifluoromethyl-phenoxy)-phenoxy]-propionyl | |
| 173 | pyrid-3-yl | H | n-propyl | ethyl | t-butyl-dimethyl-silyl | |
| 174 | pyrid-3-yl | H | ethyl | ethyl | phenyl-dimethyl-silyl | |
| 175 | pyrid-3-yl | H | ethyl | ethyl | O,O—diethylthio-phosphoryl | |
| 176 | pyrid-3-yl | H | n-propyl | ethyl | 2-methylbenzoyl | 2.60 (s), 7.4 (m), 8.65 (m) |
| 177 | 4a,7,8,8a-tetra-hydro-2H,5H—pyrano-[4,3-b]pyran-3-yl | H | n-propyl | ethyl | benzoyl | |
| 178 | 4a,7,8,8a-tetra-hydro-2H,5H—pyrano-[4,3-b]pyran-3-yl | H | n-propyl | ethyl | 2-methylbenzoyl | |
| 179 | 4a,7,8,8a-tetra-hydro-2H,5H—pyrano-[4,3-b]pyran-3-yl | H | n-propyl | ethyl | stearyl | |
| 180 | 4a,7,8,8a-tetra-hydro-2H,5H—pyrano-[4,3-b]pyran-3-yl | H | n-propyl | ethyl | 3-(2-chloro-4-trifluoro-methylphenoxy)-6-nitrobenzoyl | |
| 181 | 4a,7,8,8a-tetra-hydro-2H,5H—pyrano-[4,3-b]pyran-3-yl | H | n-propyl | ethyl | acetyl | |
| 182 | 3,4,4a,7,8,8a-hexa-hydro-2H,5H—pyrano-[4,3-b]pyran-3-yl | H | n-propyl | ethyl | benzoyl | |
| 183 | cyclohexen-4-yl | H | n-propyl | ethyl | benzoyl | |
| 184 | 4-methylcyclohex-1-en-5-yl | H | n-propyl | ethyl | benzoyl | 0.85 (t), 5.62 (s), 8.18 (d) |
| 185 | 2-methyl-1-cyclo-hexenyl | H | ethyl | ethyl | benzoyl | |
| 186 | 2,6,6-trimethyl-1-cyclohexenyl | H | n-propyl | ethyl | benzoyl | 0.5 (t), 1.75 (s), 8.05 (d) |
| 187 | 2,6,6-trimethyl-1-cyclohexenyl | H | n-propyl | allyl | benzoyl | 1.05 (s), 4.50 (d), 7.6 (d) |
| 188 | cyclododeca-4,8-dienyl | H | n-propyl | allyl | benzoyl | |
| 189 | cyclododeca-4,8-dienyl | H | ethyl | ethyl | benzoyl | 1.05 (t), 5.30 (m), 7.50 (m) |
| 190 | cyclohexyl | H | n-propyl | ethyl | benzoyl | 1.10 (t), 1.75 (m), 7.50 (m) |
| 191 | 4-methyl-cyclohex-3-enyl | H | n-propyl | ethyl | benzoyl | 0.85 (t), 1.65 (s), 5.35 (s) |
| 192 | 4-methyl-cyclohex-3-enyl | H | n-propyl | allyl | benzoyl | |
| 193 | 4-methyl-cyclohex-3-enyl | H | n-propyl | 3-chloro-allyl | benzoyl | |
| 194 | 4-methyl-cyclohex-3-enyl | H | n-propyl | ethyl | 2-methylbenzoyl | 1.10 (t), 2.60 (t), 5.35 (s) |
| 195 | 2,6,6-trimethylbicyclo-[3.1.1]heptan-3-yl | H | n-propyl | ethyl | benzoyl | 1.38 (q), 3.98 (q), 7.46 (m) |
| 196 | 2-methoxytetrahydro-pyran-5-yl | H | n-propyl | ethyl | benzoyl | |
| 197 | 2-methoxytetrahydro-pyran-5-yl | H | n-propyl | allyl | benzoyl | |
| 198 | 4-methyltetrahydro-pyran-3-yl | H | n-propyl | ethyl | benzoyl | |
| 199 | 4-methyltetrahydro-pyran-3-yl | H | n-propyl | ethyl | 2-[4-(4-trifluoromethyl-phenoxy)-phenoxy]-propionyl | |

-continued

| Compound no. | R¹ | X | R² | R³ | A | ¹H—NMR data |
|---|---|---|---|---|---|---|
| 200 | 4-methyltetrahydro-pyran-3-yl | H | n-propyl | ethyl | 2-[4-(4-iodopyrid-2-yloxy)-phenoxy]-propienyl | |
| 201 | tetrahydrofuran-3-yl | H | n-propyl | ethyl | benzoyl | |
| 202 | 5,6-dihydro-2H—pyran-3-yl | H | n-propyl | ethyl | benzoyl | |
| 203 | 2-methoxytetrahydro-pyran-6-yl | H | n-propyl | ethyl | benzoyl | 1.05 (t), 3.32 (s), 4.70 (s) |
| 204 | tetrahydropyran-3-yl | COOCH₃ | n-propyl | ethyl | benzoyl | 0.88 (t), 3.75 (m), 7.45 (t) |
| 205 | 2-methylpyrid-6-yl | H | n-propyl | ethyl | benzoyl | 1.08 (t), 2.55 (s), 8.05 (d) |
| 206 | pyrid-4-yl | H | n-propyl | ethyl | benzoyl | 3.60 (m), 4.0 (q), 7.28 (m) |
| 207 | 1-oxotetrahydro-thiopyran-3-yl | H | ethyl | ethyl | benzoyl | 1.85 (m), 3.45 (m), 4.00 (q) |
| 208 | 1-oxotetrahydro-thiopyran-3-yl | H | n-propyl | ethyl | benzoyl | |
| 209 | 1,1-dioxotetrahydro-thiopyran-3-yl | H | n-propyl | ethyl | benzoyl | |
| 210 | 1,1-dioxotetrahydro-thiopyran-3-yl | H | ethyl | ethyl | benzoyl | 1.05 (t), 4.0 (q), 8.0 (d) |
| 211 | 1-benzyloxyethyl | H | n-propyl | ethyl | benzoyl | 0.90 (t), 3.55 (m), 7.35 (s) |
| 212 | 1-[2-n-butoxy)-ethoxy]ethyl | H | n-propyl | ethyl | benzoyl | 3.60 (m), 4.0 (q), 7.60 (m) |
| 213 | 2-[2-(n-butoxy)-ethoxy]ethyl | H | n-propyl | ethyl | benzoyl | |
| 214 | 4-fluorophenyl | H | n-butyl | ethyl | benzoyl | 1.35 (m), 4.0 (q), 7.05 (t) |
| 215 | 3-methyl-4-methoxy-phenyl | H | n-propyl | ethyl | benzoyl | 2.14 (s), 3.88 (s), 8.10 (m) |
| 216 | 3-methyl-phenyl | H | ethyl | ethyl | benzoyl | |
| 226 | 2-i-propyl(-1,3-di-oxepan)-5-yl | H | n-propyl | ethyl | benzoyl | |
| 227 | 2-i-propyl(-1,3-di-oxepan)-5-yl | H | ethyl | ethyl | benzoyl | |
| 228 | tetrahydropyran-3-yl | H | n-propyl | ethyl | 2-(4-chlorophenyl)-2-methyl-propionyl | 1.61 (s), 4.08 (q), 7.31 (m) |
| 229 | tetrahydropyran-3-yl | H | n-propyl | ethyl | 2-methyl-fur-3-yl-carbonyl | 2.60 (s), 3.23 (q), 6.65 (s) |
| 230 | tetrahydropyran-3-yl | H | n-propyl | ethyl | 2-(2,4,5-trichloro-phenoxy)-propionyl | 4.85 (m), 7.01 (s), 7.52 (s) |
| 231 | 4-methylcyclohex-1-en-5-yl | H | n-propyl | allyl | benzoyl | 0.85 (t), 4.45 (d), 5.60 (s) |
| 232 | 4-methylcyclohex-1-en-5-yl | H | n-propyl | ethyl | methylsulfonyl | 1.30 (t), 3.25 (s), 6.67 (s) |
| 233 | 4-methylcyclohex-1-en-5-yl | H | ethyl | ethyl | benzoyl | 1.10 (t), 7.50 (m), 8.05 (d) |
| 234 | 4-methylcyclohex-1-en-5-yl | H | ethyl | ethyl | methylsulfonyl | 1.25 (t), 3.2 (s), 5.65 (s) |
| 235 | 4-methylcyclohex-1-en-5-yl | H | ethyl | allyl | benzoyl | |
| 236 | 2-ethylthio-n-propyl | H | n-propyl | ethyl | 2-(2,4,5-trichloro-phenoxy)-propionyl | 4.10 (9), 7.00 (s), 7.52 (s) |
| 237 | 2-ethylthio-n-propyl | H | n-propyl | ethyl | 2-(3-bromophenoxy)-phenoxy)-propionyl | 4.05 (q), 4.81 (q), 7.10 (m) |
| 238 | 2-ethylthio-n-propyl | H | n-propyl | ethyl | 2-(4-bromophenyl)-propionyl | 2.5 (m), 7.26 (m), 7.46 (m) |
| 239 | 2-ethylthio-n-propyl | H | n-propyl | ethyl | 2-(4-fluorophenyl)-propionyl | 1.55 (d), 4.05 (m), 7.04 (m) |
| 240 | 5,6-dihydro-2H—1-oxo-thiopyran-3-yl | H | n-propyl | 3-chloro-allyl | benzoyl | 0.85 (t), 3.60 (m), 7.55 (m) |
| 241 | 2-ethylthio-n-propyl | H | n-propyl | ethyl | O,O—diethylphosphoryl | 0.95 (t), 2.58 (q), 4.2 (m) |
| 242 | 2-ethylthio-n-propyl | H | n-propyl | ethyl | n-butyl-dimethyl-silyl | 0.08 (s), 1.3 (m), 2.9 (m) |
| 243 | 2-ethylthio-n-propyl | H | n-propyl | ethyl | phenyl-dimethyl-silyl | 0.35 (s), 1.0 (t), 7.4 (m) |
| 244 | tetrahydropyran-3-yl | H | n-propyl | ethyl | O,O—diethylthio-phosphoryl | 0.90 (t), 1.40 (t), 4.10 (q) |
| 245 | tetrahydropyran-3-yl | H | n-propyl | ethyl | O,O—diethylphosphoryl | 0.95 (t), 1.38 (t), 4.2 (m) |
| 246 | tetrahydropyran-3-yl | H | n-propyl | ethyl | n-butyl-dimethyl-silyl | |
| 247 | tetrahydropyran-3-yl | H | n-propyl | ethyl | phenyl-dimethyl-silyl | 0.30 (s), 0.93 (t), 6.35 (m) |
| 248 | 2-ethylthio-n-propyl | H | n-propyl | ethyl | | |
| 249 | 4-methyltetrahydro-pyran-3-yl | H | n-propyl | 3-chloro-allyl | O,O—diethylthio-phosphoryl | 0.92 (t), 1.37 (t), 4.7 (m) |
| 250 | 4-methyltetrahydro-pyran-3-yl | H | n-propyl | 3-chloro-allyl | O,O—diethylphosphoryl | 0.95 (t), 1.4 (t), 6.15 (m) |
| 251 | 4-methyltetrahydro-pyran-3-yl | H | n-propyl | 3-chloro-allyl | phenyl-dimethyl-silyl | 0.62 (s), 5.08 (d), 7.63 (m) |
| 252 | 4-methyltetrahydro-pyran-3-yl | H | n-propyl | 3-chloro-allyl | 2-[4-(4-trifluoromethyl-phenoxy)-phenoxy]-propionyl | 1.0 (d), 3.4 (t), 7.0 (m) |
| 253 | 2-(4-chlorophenyl-thio)-ethyl | H | ethyl | ethyl | 4-chlorobenzoyl | 1.10 (t), 1.80 (q), 2.97 (t), 7.26 (s) |
| 254 | tetrahydropyran-3-yl | H | n-propyl | ethyl | benzyl | 0.90 (t), 1.30 (m), 5.10 (s), 7.35 (m) |

-continued

| Compound no. | R¹ | X | R² | R³ | A | ¹H—NMR data |
|---|---|---|---|---|---|---|
| 255 | 5,6-dihydro-2H—1,1-dioxothiopyran-3-yl | H | n-propyl | 3-chloro-allyl | benzoyl | 0.88 (t), 3.60 (m), 7.55 (m) |
| 256 | pyridyl-3-yl | H | n-propyl | ethyl | pivaloyl | |
| 257 | 5,6-dihydro-2H—1-oxothiopyran-3-yl | H | n-propyl | ethyl | benzoyl | |
| 258 | 4a,7,8,8a-tetrahydro-2H,5H—pyrano-[4,3-b]-3-yl | H | n-propyl | allyl | benzoyl | |
| 263 | pyrid-3-yl | H | n-propyl | ethyl | 2,5-dichloro-6-methoxy-benzoyl | 0.90 (t), 3.90 (m), 8.60 (m) |
| 264 | 4-methylcyclohex-1-en-5-yl | H | n-propyl | ethyl | benzoyl | 0.85 (t), 3.98 (q), 8.05 (d) |
| 265 | cyclododecyl | H | n-propyl | ethyl | benzoyl | 0.90 (t), 3.97 (q), 8.04 (d) |
| 266 | tetrahydrofur-3-yl | H | n-propyl | ethyl | benzoyl | 0.85 (t), 3.85 (q), 7.50 (m) |
| 267 | tetrahydrothiopyran-3-yl | H | n-propyl | ethyl | O,O—diethylthiophosphoryl | 0.92 (t), 1.4 (m), 4.2 (m) |
| 268 | tetrahydropyran-4-yl | H | n-propyl | ethyl | benzoyl | |
| 269 | tetrahydropyran-4-yl | H | n-propyl | ethyl | palmitoyl | |
| 270 | tetrahydropyran-4-yl | H | n-propyl | ethyl | stearoyl | |
| 271 | tetrahydropyran-4-yl | H | n-propyl | ethyl | 3-(2-chloro-4-trifluoromethyl-phenoxy)-6-nitrobenzoyl | |
| 272 | tetrahydropyran-4-yl | H | ethyl | ethyl | 3-(2-chloro-4-trifluoromethyl-phenoxy)-6-nitrobenzoyl | |
| 273 | tetrahydropyran-4-yl | H | ethyl | allyl | 3-(2-chloro-4-trifluoromethyl-phenoxy)-6-nitrobenzoyl | |
| 274 | tetrahydropyran-4-yl | H | n-propyl | ethyl | 2-[4-(4-trifluoromethyl-phenoxy)-phenoxy]-propionyl | |
| 275 | tetrahydropyran-4-yl | H | n-propyl | ethyl | 2-[4-(4-iodopyrid-2-yloxy)-phenoxy]-propionyl | |
| 276 | tetrahydropyran-4-yl | H | n-propyl | ethyl | 2-[4-(4-trifluoromethylpyryl-2-yloxy)-phenoxy]O,O— | |
| 277 | tetrahydropyran-4-yl | H | n-propyl | ethyl | 2-[4-(4-trifluoromethyl-6-chloro-pyrdi-2-yloxy)-phenoxy]-propionyl | |
| 278 | tetrahydropyran-4-yl | H | n-propyl | ethyl | 2-[4-(6-chloro-2-quinoxalinoxy)-phenoxy]-propionyl | |
| 279 | tetrahydropyran-4-yl | H | n-propyl | ethyl | 2-[4-(6-chlorobenzthiazol-2-yloxy)-phenoxy]-propionyl | |
| 280 | tetrahydropyran-4-yl | H | n-propyl | ethyl | 2-[4-(6-chlorobenzoxazol-2-yloxy)-phenoxy]-propionyl | |
| 281 | 6-methoxy-tetrahydropyran-2-yl | H | ethyl | ethyl | benzoyl | |
| 282 | 3,4,4a,7,8,8a-hexahydro-2H,5H—pyrano-[4,3-b]pyran-3-yl | H | n-propyl | allyl | benzoyl | 0.90 (t), 4.4 (d), 8.15 (d) |

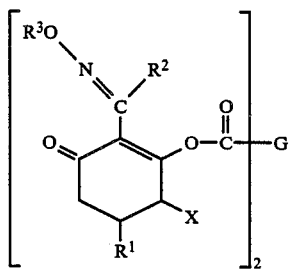

| Compound no. | R¹ | X | R² | R³ | G | ¹H—NMR data |
|---|---|---|---|---|---|---|
| 218 | tetrahydropyran-3-yl | H | n-propyl | ethyl | phenylene | 0.90(t), 1.08(t), 8.17(s) |
| 219 | tetrahydropyran-3-yl | H | n-propyl | ethyl | propylene | 0.90(t), 1.70(s), 3.90(m) |
| 220 | tetrahydropyran-3-yl | H | n-propyl | ethyl | tetramethylene | |
| 221 | tetrahydropyran-3-yl | H | n-propyl | ethyl | hexamethylene | |
| 222 | tetrahydrothiopyran-3-yl | H | n-propyl | ethyl | phenylene | |
| 223 | tetrahydrothiopyran-3-yl | H | n-propyl | ethyl | methylene | |
| 224 | tetrahydrothiopyran-3-yl | H | n-propyl | ethyl | tetramethylene | |

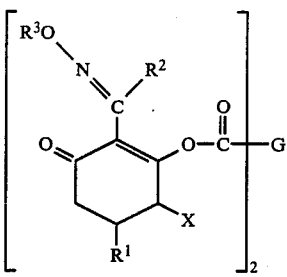

| Compound no. | R¹ | X | R² | R³ | G | ¹H—NMR data |
|---|---|---|---|---|---|---|
| 225 | pyrid-3-yl | H | n-propyl | ethyl | tetramethylene | |
| 259 | 4a,7,8,8a-tetra-hydro-2H,5H—pyrano-[4,3-b]-3-yl | H | n-propyl | ethyl | phenylene | |
| 260 | 4a,7,8,8a-tetra-hydro-2H,5H—pyrano-[4,3-b]-3-yl | H | n-propyl | ethyl | tetramethylene | |
| 261 | 2-i-propyl-1,3-dioxepan-5-yl | H | n-propyl | ethyl | phenylene | |
| 262 | 2-i-propyl-1,3-dioxepan-5-yl | H | ethyl | ethyl | phenylene | |

The cyclohexenol derivatives of the formula I may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, and N-methylpyrrolidone, and water are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

Examples of formulations are given below.

I. 90 parts by weight of compound no. 2 is mixed with 10 parts by weight of N-methyl-alpha-pyrrolidone. A mixture is obtained which is suitable for application in the form of very fine drops.

II. 20 parts by weight of compound no. 8 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 5 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 253 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 60 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 109 is intimately mixed with 97 parts by weight of particulate kaolin. A dust is obtained containing 3% by weight of the active ingredient.

VII. 30 parts by weight of compound no. 252 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts of compound no. 1 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients, or agents containing them, may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The amount of active ingredient applied depends on the time of the year, the plants to be combated and their growth stage, and varies from 0.025 to 3 kg/ha, but is preferably from 0.1 to 1.5 kg/ha.

The action of the cyclohexenol derivatives of the formula I on plant growth is demonstrated in greenhouse experiments.

The vessels employed were plastic flowerpots having a volume of 300 cm³, and which were filled with a sandy loam containing about 1.5% humus. The seeds of the test plants were sown shallow, and separately, according to species. For the preemergence treatment, the active ingredients were applied to the surface of the soil immediately after the seeds had been sown. The compounds were emulsified or suspended in water as vehicle, and sprayed through finely distributing nozzles. The application rate was 3.0 kg of active ingredient per hectare. After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the active ingredients.

For the postemergence treatment, the plants were first grown in the vessels to a height of from 3 to 15 cm, depending on growth form, before being treated. The soybean plants were grown in a peat-enriched substrate. For this treatment, either plants which had been sown directly in the pots and grown there were selected, or plants which had been grown from seedlings and were transplanted to the pots a few days before treatment. The application rates for postemergence treatment were 0.125, 0.25, 0.5 and 3.0 kg of active ingredient per hectare. No covers were placed on the pots in this treatment.

The pots were set up in the greenhouse—species from warmer areas at from 20° to 35° C., and species from moderate climates at 10° to 25° C. The experiments were run for 2 to 4 weeks. During this period, the plants were tended and their reactions to the various treatments assessed. The scale used for assessment was 0 to 100, 0 denoting no damage or normal emergence, and 100 denoting nonemergence of complete destruction of at least the visible plant parts.

The plants used in the experiments were *Alopecurus myosuroides, Avena fatua, Avena sativa, Beta vulgaris, Brassica napus,* Bromus spp., Cassia spp., *Digitaria sanguinalis, Echinochloa crus-galli, Eleusine indica, Glycine max., Gossypium hirsutum, Helianthus annuus, Hordeum vulgare,* Ipomoea spp., *Lolium multiflorum, Setaria italica, Sinapis alba, Sorghum bicolor, Sorghum halepense, Triticum aestivum,* and *Zea mays.*

PREEMERGENCE APPLICATION

For examples compounds nos. 39, 229, 109, 207, 210, 55, 53, 161, 12, 2, 8, 61, 60, 160, 252, 250 and 242 proved to be herbicidally effective on plants from the Gramineae family, whereas mustard (*Sinapis alba*), a dicotyledonous member of the Cruciferae family, remained completely undamaged. On the other hand, compounds nos. 73, 230, 25 and 72, on preemergence application, controlled both the grassy plants tested and the broadleaved plant mustard.

POSTEMERGENCE APPLICATION

For example compounds nos. 217, 28, 30, 22, 191, 79, 37, 239, 17 and 228, applied postemergence at a rate of 3.0 kg/ha, controlled grassy plants. Compounds nos. 230, 26, 73 and 72 had an action both on grassy and broadleaved plants.

On application of 0.125 kg/ha, for instance compounds nos. 109, 207, 252, 40, 20, 238, 71, 74, 35, 56, 186, 255, 122, 29, 176, 33, 190, 206, 169, 7, 5, 13, 219, 254, 9, 27, 31, 18, 32, 24, 57, 42 and 266, and for example compounds nos. 1, 2, 4, 5, 241, 242, 243, 245 und 247 applied at a rate of 0.25 kg/ha were extremely effective on plants from the Gramineae family, Compound no. 253, at 0.125 kg/ha, also controlled unwanted grassy plants without damaging broadleaved crops. Unwanted grassy species were selectiely combatted in a cereal crop wheat, which is also a member of the Gramineae family, by 0.25 kg/ha of compound no. 61. Further, for instance compounds nos. 194, 212, 233 and 234 controlled unwanted grasses in cereals.

In view of the broad spectrum of weeds combatted, the tolerance by crop plants and the numerous application methods possible, the compounds according to the invention may be used in a large number of crop plants.

The following crops may be mentioned by way of example:

| Botanical name | Common name |
|---|---|
| Allium cepa | onions |
| Ananas comosus | pineapples |
| Arachis hypogaea | peanuts (groundnuts) |
| Asparagus officinalis | asparagus |
| Beta vulgaris spp. altissima | sugarbeets |
| Beta vulgaris spp. rapa | fodder beets |
| Beta vulgaris spp. esculenta | table beets, red beets |
| Brassica napus var. napus | rapeseed |
| Brassica napus var. napobrassica | swedes |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermudagrass in turf and lawns |
| Daucus carota | carrots |
| Elais guineensis | oil palms |
| Fragaria vesca | strawberries |
| Glycine max | soybeans |
| Gossypium hirsutum (Gossypium arboreum Gossypium herbaceum Gossypium vitifolium) | cotton |
| Helianthus annuus | sunflowers |
| Helianthus tuberosus | Jerusalem artichoke |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicothiana tabacum (N. rustica) | tobacco |
| Olea europaea | olive trees |
| Oryza sativa | rice |
| Panicum miliaceum | millet |
| Phaseolus lunatus | limabeans |
| Phaseolus mungo | mungbeans |
| Phaseolus vulgaris | snapbeans, green beans, dry beans |
| Petroselinum crispum spp. tuberosum | parsley |
| Picea abies | Norway spruce |
| Abies alba | fir trees |
| Pinus spp. | pine trees |
| Pisum sativum | English peas |

-continued

| Botanical name | Common name |
|---|---|
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |
| Spinacia oleracea | spinach |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize (post-directed) |

To increase the spectrum of action and to achieve synergistic effects, the novel cyclohexenol derivatives may be mixed and applied together with numerous representatives of other herbicidal or growth-regulating active ingredient groups. Examples of suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, quinolinecarboxylic acids, etc.

It may also be useful to apply the cyclohexenol derivatives of the formula I, or herbicidal agents containing them, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

We claim:

1. A cyclohexenol derivative of the formula I

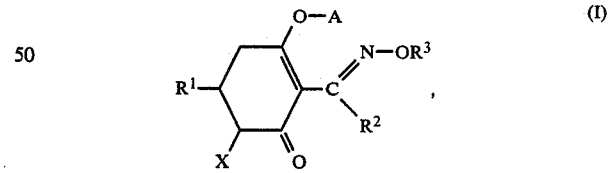

wherein $R_1$ is a tetrahydropyran, a tetrahydrothiopyran, a 1-oxo-tetrahydrothiopyran, or a 1,1-dioxo-tetrahydrothiopyran radical, X is hydrogen wherein $R^1$ is a pyran or thiopyran radical, is hydrogen or methoxycarbonyl, $R^2$ is alkyl of 1 to 4 carbon atoms, $R^3$ is alkyl of 1 to 3 carbon atoms, alkenyl of 3 or 4 carbon atoms, haloalkenyl of 3 or 4 carbon atoms and 1 to 3 halogen substituents, or propargyl, and A is a radical of the general structure DE, where D is methylene, CO or $SO_2$ and E is an alkyl or alkenyl radical of not more than 20 carbon atoms, unsubstituted or methyl-substituted cycloalkyl of not more than 6 carbon atoms, or styryl, or is a phenyl or benzyl radical which is unsubstituted or substituted by not more than 3 substituents from the group consisting of halogen, $C_1$–$C_4$-alkyl, $C_1$–$C_4$-alkoxy and nitro, or is a 1-methylbenzyl or 1,1-dimethylbenzyl radical which is unsubstituted or substituted by halogen or methoxy, or is haloalkyl of note more than 3 carbon atoms and not more than 3 halogen atoms, alkoxymethyl, acetoxymethyl or alkoxycarbonylalkyl, or is phenoxyalkyl which is unsubstituted or substituted in the phenoxy moiety by not more than 3 substituents from the group consisting of halogen, alkyl, alkoxy and methylsulfonyl, and which possesses a straight-chain or branched alkylene chain of not more than 5 carbon atoms, or A is a radical of the formula

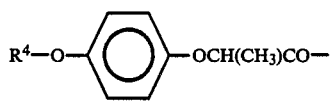

where $R^4$ is phenyl which is substituted by trifluoromethyl, halogen or $C_1$–$C_4$-alkyl, or A is a radical of the formula

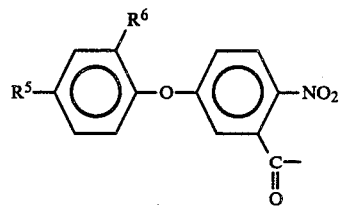

where $R^5$ and $R^6$ are each halogen or $CF_3$.

2. A cyclohexenol derivative of the formula I as defined in claim 1, where X is hydrogen.

3. A cyclohexenol derivative of the formula I as defined in claim 1, where $R^1$ is tetrahydropyranyl, tetrahydrothiopyranyl, 1-oxotetrahydrothiopyranyl or 1,1-dioxotetrahydrothiopyranyl.

4. A cyclohexanol derivative(I) as defined in claim 1, wherein $R^1$ is tetrahydropyran.

5. A cyclohexenol derivative of the formula I as claimed in claim 1, where $R^1$ is tetrahydrothiopyran-3-yl.

6. A cyclohexenol derivative of the formula I as defined in claim 1, where $R^1$ is tetrahydrothiopyran-3-yl, $R^2$ is n-propyl, $R^3$ is ethyl, X is hydrogen, and A is benzoyl.

7. A cyclohexanol derivative of the formula I as defined in claim 1, where $R^1$ is tetrahydrothiopyran-3-yl, $R^2$ is n-propyl, $R^3$ is ethyl, X is hydrogen, and A is 2-[4-(4-trifluoromethylphenoxy)-phenoxy]-propionyl.

8. A cyclohexenol derivative of the formula I as defined in claim 1, wherein A is benzoyl.

9. A cyclohexenol derivative of the formula I as defined in claim 1, wherein A is 2-[4-(4-trifluoromethylphenoxy)-phenoxy]-propionyl.

10. A herbicidal composition containing an inert carrier and a herbicidally effective amount of a cyclohexenol derivative as defined in claim 1.

11. A herbicidal composition containing an inert carrier and a herbicidally effective amount of a cyclohexenol derivative of the formula I as defined in claim 2.

12. A herbicidal composition containing an inert carrier and a herbicidally effective amount of a cyclohexenol derivative of the formula I as defined in claim 3.

13. A process for controlling the growth of unwanted grassy plants, wherein the unwanted plants and/or the area to be kept free from unwanted plant growth are treated with a herbicidally effective amount of a cyclohexenol derivative of the formula I as defined in claim 1.

14. A process for controlling the growth of unwanted grassy plants, wherein the unwanted plants and/or the area to be kept free from unwanted plant growth are treated with a herbicidally effective amount of a cyclohexenol derivative of the formula I as defined in claim 8.

15. A process for controlling the growth of unwanted grassy plants, wherein the unwanted plants and/or the area to be kept free from unwanted plant growth are treated with a herbicidally effective amount of a cyclohexenol derivative of the formula I as defined in claim 9.

* * * * *